United States Patent
Ueno et al.

(10) Patent No.: US 6,562,998 B1
(45) Date of Patent: May 13, 2003

(54) GRANULES OF 2-HYDROXYNAPHTHALENE-3-CARBOXYLIC ACID AND METHOD FOR PREPARING THE SAME

(75) Inventors: Ryuzo Ueno, Nishinomiya (JP); Masaya Kitayama, Takarazuka (JP); Nobutaka Izumichi, Ashiya (JP); Syungo Nara, Kawanishi (JP); Masaharu Kittaka, Takarazuka (JP)

(73) Assignee: Kabushiki Kaisha Ueno Seiyako Oyo Kenkyujo, Osaka (JP)

( * ) Notice: Subject to any disclaimer, the term of this patent is extended or adjusted under 35 U.S.C. 154(b) by 35 days.

(21) Appl. No.: 09/869,143

(22) PCT Filed: Oct. 19, 2000

(86) PCT No.: PCT/JP00/07260

§ 371 (c)(1),
(2), (4) Date: Jun. 26, 2001

(87) PCT Pub. No.: WO01/30737

PCT Pub. Date: May 3, 2001

(30) Foreign Application Priority Data

Oct. 26, 1999 (JP) ............................................ 11-303833

(51) Int. Cl.$^7$ .......................... C07C 63/34; C07C 63/00
(52) U.S. Cl. ...................... 562/467; 562/400; 562/405; 562/465; 562/466; 562/487; 562/480
(58) Field of Search ................. 562/487, 400, 562/485, 405, 465, 466, 467

(56) References Cited

FOREIGN PATENT DOCUMENTS

| GB | 2008090 | 5/1979 |
| JP | 59-196841 | 11/1984 |
| JP | 59196841 A | * 11/1984 |
| JP | 61-212533 | 9/1986 |
| JP | 5-294862 | 11/1993 |
| JP | 11-43462 | 2/1999 |
| JP | WO/0068177 | * 11/2000 |
| WO | 00/68177 | 11/2000 |

* cited by examiner

Primary Examiner—Alan L. Rotman
Assistant Examiner—Héctor M Reyes
(74) Attorney, Agent, or Firm—Sughrue Mion, PLLC

(57) ABSTRACT

Granular product of 2-hydroxynaphthalene-3-carboxylic acid with well-suppressed dusting tendency, and process for preparing the same is provided.

Granular product of 2-hydroxynaphthalene-3-carboxylic acid having an average particle size of 150 $\mu$m or more and a hardness of 70–3000 g, and a process for preparing the same comprising the steps of dry compressing powdery 2-hydroxynaphthalene-3-carboxylic acid to give compressed material and pulverizing and classifying the same.

9 Claims, No Drawings

GRANULES OF 2-HYDROXYNAPHTHALENE-3-CARBOXYLIC ACID AND METHOD FOR PREPARING THE SAME

TECHNICAL FIELD

The present invention provides a granular product of 2-hydroxynaphthalene-3-carboxylic acid having significantly suppressed dusting tendency, and a process for preparing the same.

BACKGROUND ART 2-hydroxynaphthalene-3-carboxylic acid is important as an intermediate for pigments or dyes. Generally, the compound is synthesized by reacting β-naphthol with sodium hydride to give sodium β-naphtholate, reacting the resulting compound with carbon dioxide under pressure to give sodium 2-hydroxynaphthalene-3-carboxylate and then, isolating the desired compound by means of acid precipitation i.e. by adding a mineral acid to the salt.

For a long time, the Kolbe-Schmitt reaction, a solid-gas phase reaction, had been employed for the reaction between sodium β-naphtholate and carbon dioxide. Said reactions however, has some problems such as more than 50 hours of long reaction time, high amount of wasted β-naphthol because of thermal heterogeneity at the high reaction temperature and difficulties in controlling the reaction due to the phase conversion, and a stable yield can be hardly obtained. In order to solve those problems, a number of methods including a method using a reaction medium had been proposed.

One of the present inventors had invented a process comprising the step of reacting a liquid mixture consisting of light oil or kerosene, sodium β-naphtholate and β-naphthol, with carbon dioxide (Japanese Patent Publication (KOKOKU) No. 53296/11981) and said process has been industrially used. This process can be carried out successively and can provide 2-hydroxynaphthalene-3-carboxylic acid with very low amount of impurities and with highly stable quality. According to said method, 2-hydroxynaphthalene-3-carboxylic acid with high quality, such as those having 220–221° C. of melting point and 99.5% of purity and containing only 0.03% of sodium β-naphtholate, can be obtained. In the process, 2-hydroxynaphthalene-3-carboxylic acid is isolated from the mother liquid by means of acid precipitation, filtration, centrifugation and the like, washed with water, dried and then, is used as an intermediate for pigments or dyes.

Crystalline product of 2-hydroxynaphthalene-3-carboxylic acid usually comprises very fine particles and, therefore, is highly dusty. In addition to the dust, due to the severe mucosal irritativeness of 2-hydroxynaphthalene-3-carboxylic acid, handling of the compound is highly obstructed. For example, when 2-hydroxynaphthalene-3-carboxylic acid is added into a reaction vessel as an intermediate for a pigment or dye, fine particles of 2-hydroxynaphthalene-3-carboxylic acid fly in the air as powdery dust. The fine particles of 2-hydroxynaphthalene-3-carboxylic acid flown in the air are hardly precipitated. They disperse widely, pollute the environment, and stimulate the skin and mucosa of the operators to make them uncomfortable. In order to diminish the problems concerning workability and safety in the feeding step, operators wear dust-proof glasses and masks and the reactor is mounted a vacuum at a position other than the supply port and a filter to trap the fine particles. However, they are not enough.

The reason why 2-hydroxynaphthalene-3-carboxylic acid dusts significantly is believed that said compound consists of very fine crystalline particles, and that said compound is hardly dissolved in water and, therefore, hardly uptakes moisture; and therefore, each crystalline particles do not agglomerate or bind together through water of adhesion. As a consequence, the fine crystalline particles move individually upon an external impact.

Further, when fine particles of 2-hydroxynaphthalene-3-carboxylic acid are added to a medium, the particles tend to agglomerate to lower the solubility of the same which deteriorate the operability.

In order to suppress the dust of the material having the above-described characteristics, Japanese patent Application Laid Open No. 196841/1983 discloses granular product prepared by a wet extrusion granulating process comprising steps of kneading 2-hydroxynaphthalene-3-carboxylic acid particles having a certain particle properties and containing 13–30% of water, granulating the same by means of extrusion granulator and drying. Thus obtained granules are made of small particles which are attracted each other with relatively low bonding force, and tends to be degraded during transporting or forwarding the granules to give original small particles which is highly dusty.

Further, said process requires complicated steps such as adding a certain amount of water to the dry particles and controlling moisture content of acid precipitated 2-hydroxynaphthalene-3-carboxylic acid particles by means of centrifugation or the like, and therefore, is not suitable for large scale production.

In the field of pharmaceutical preparation, it is proposed that good granular product may be obtained by adding binder component such as dextrin, starch and carboxymethyl cellulose to the base component as well as water or alcohol, kneading and granulating the same. However, if a binder component is added during preparation of 2-hydroxynaphthalene-3-carboxylic acid, high purity product cannot be obtained and the azo pigment or molded polymer prepared with the product might have imposed color tone or deteriorated properties.

Accordingly, the object of the present invention is to solve the above-mentioned problems and to provide granular product of 2-hydroxynaphthalene-3-carboxylic acid with well-suppressed dusting tendency.

DISCLOSURE OF INVENTION

The present invention provides granular product of 2-hydroxynaphthalene-3-carboxylic acid having an average particle size of equal to or more than 150 μm and a hardness of 70–3000 g. The granular product of the present invention exhibits well suppressed dusting tendency and therefore, is easy to handle and the affects little to environment and human beings. In addition, the granular product of 2-hydroxynaphthalene-3-carboxylic acid is strong enough to resist against fairly strong impact such that it is not degraded to the original fine particles by certain impact. Therefore degradation of the product during transportation or the like is well suppressed. Further, despite the large average particle size of over 150 μm, the granular product of the present invention exhibits excellent dissolution property, which is even superior to that of conventional powdery product having a small particle size (40–70μm) and therefore is useful as an intermediate for preparing dyes and pigments.

The granular product of the present invention may be prepared by a method comprising the steps of, dry compressing powdery 2-hydroxynaphthalene-3-carboxylic acid to give a compressed material, pulverizing and classifying the same. Accordingly, the method for preparing the granular product is also in the scope of the present invention.

DEFINITIONS

Average Particle Size

An average particle size represents the value measured as follows:

A sample product is weighted and then is sequentially screened with sieves having aperture of 1180 μm, 500 μm, 297 μm, 180 μm, 106 μm and 74 μm in this order. Firstly, the weighted sample product is screened with the sieve having aperture of 1180 μm at 230 rpm for 10 minutes. The amount of the residues on the sieve was weighted and the weight ratio (wt %) to the starting amount is calculated. The sample passed through the 1180 μm sieve was then screened with the sieve having aperture of 500 μm in the same manner as above. These steps repeated successively and at the last, the amount of the product passed through the 74 μm sieve is weighed. The average particle size is the value calculated as follows:

average particle size (μm)=(1180× residue on the 1180 μm sieve (wt %)/100)+(500× residue on the 500 μm sieve (wt %)/100)+(297× residue on the 297 μm sieve (wt %)/100)+(106× residue on the 106 μm sieve (wt %)/100)+(74× residue on the 74 μm sieve (wt %)/100)+(45× passed the

74 μm sieve (wt %)/100).

Hardness

Hardness is measured by the simplified granular hardness meter. The granular sample is applied load by means of a conical push-bar with 1 mmΦ head and the weight at where the sample is broken is taken for hardness of the sample.

Degradation Ratio Test Measured by Defacement Tester.

The degradation ratio test determines degradability of a granular product. 10 g of the sample product is sieved with 60M-mesh screen (sieve having aperture of 0.25 mm) at 230 rpm for 1 minute. The residue on the sieve is loaded into defacement tester having inner diameter of 27 cm and thickness of 4 cm and is subjected to impact stress at 25 rpm for 3 minutes. Thus treated sample is sieved again with the 60M-mesh screen for 1 minute. The degradation ratio (%) is calculated with the amount of residue on the mesh before loading impact stress ($W_1$) and those after loading impact stress ($W_2$) according to the following formula:

Degradation ratio (%)=($W_1$–$W_2$)/$W_1$×100

Angle of repose, aerated bulk density and packed bulk density are determined by means of Powder Tester (Type PT-N), Hosokawa micron Co. according to the manufacturers instruction.

Angle of Repose

Sample is shaken on the standard sieve (10 mesh) to allow falling through a funnel and the angle of repose is measured by means of the pouring method.

Aerated Bulk Density

Sample is shaken on the sieve to allow falling into a standard container through the shout, and then the standard container is weighted to determine the aerated bulk density.

Packed Bulk Density

The sample was filled into a standard container, the container is tapped from a given height for given times and then, bulk density of the sample packed by tapping impact is determined.

Compression Ratio

The compression ratio is the value obtained according to the following formula:

(packed bulk density–aerated bulk density)/packed bulk density× 100

According to the present invention, the average particle size of the granular product of 2-hydroxynaphthalene-3-carboxylic acid is equal to or more than 150 μm, preferably, 297–2000 μm, more preferably, 350–1600 μm. In case of the average particle size is less than 150 μm, satisfied dusting suppression may not be achieved and the granules may agglomerate when dissolved in a medium to give low dissolution rate. In case of the average particle size is over 2000 μm, the product may exhibit well-suppressed dusting tendency, but also low dissolution rate which may cause operation problems.

According to the present invention, the granular product of 2-hydroxynaphthalene-3-carboxylic acid may contain less than 14 wt %, more preferably, less than 6 wt % of particles that pass through the 74 μm sieve. When the composition contains more than 14 wt % of the small particles that pass the 74 μm sieve, the product will dust extensively due to those small size particles.

According to the present invention, the hardness of the granular product of 2-hydroxynaphthalene-3-carboxylic acid is 70–3000 g, and preferably, 100–1000 g. When the hardness is less than 70 g, the granular product may be easily degraded during transportation or the like into fine particles, which cause dusting. When the hardness is over 3000 g, the bonding force among the particles constituting the granule is too strong to be dissolved in a medium and may cause operation problems.

The granular product of 2-hydroxynaphthalene-3-carboxylic acid may preferably be enough strong against impact or vibration stress such that it does not degrade into fine particles upon certain impact. Degradation ratio of the product measured by defacement tester, which is the index representing impact strength of the product, may be equal to or less than 3% such that the product is easy to handle in transporting and operating.

The granular product of the present invention exhibits good dissolution rate. It has been known that 2-hydroxynaphthalene-3-carboxylic acid, especially those having large crystalline size, can hardly be dissolved in water or the like, and therefore is inconvenient to employ the same in manufacturing dyes or pigments. However, the granular product obtained by the process of the present invention described below, i.e. dry milling granulation process, exhibits an excellent dissolution property than those obtained by the conventional wet extrusion granulation process. The dissolution property of the granular product of the present invention is even superior to those of powdery products having small particle sizes (40–70 μm).

The mechanism of the excellent dissolution property may be explained as follows. When the granular product of 2-hydroxynaphthalene-3-carboxylic acid according to the present invention is dissolved in a medium, the bonding force among the particles constituting the granule is decreased and the medium invade into intraparticle gaps, the bonding force disappears, and then the respective particles are dispersed. To the contrary, conventionally prepared 2-hydroxynaphthalene-3-carboxylic acid granules, that is, those prepared by using water as binder component, are hardly dispersed into smaller particles even in the medium. This is because the bonding force among the particles is kept even in a medium due to the strong surface tension of the water, and the medium can hardly invade into the intraparticle gaps. In addition, powdery 2-hydroxynaphthalene-3-carboxylic acid having a small particle size represents a certain dissolution property but is apt to agglomerate in the medium to deteriorate the solubility.

In more detail, dissolution time determined by dissolving 10 g of the granular product of 2-hydroxynaphthalene-3-carboxylic acid according to the present invention in 104 g of 5% aqueous sodium hydroxide at an ambient temperature may be less than 20 minutes, and for easy handling, preferably be less than 15 minutes. The dissolution property of the granular product of the present invention is far superior to those granular product prepared by the conventional extruding granulation or conventional powdery product having a small particle size.

In addition, the angle of repose of the granular product of 2-hydroxynaphthalene-3-carboxylic acid may be 35–45°, preferably, 37–43°. This range of the angle of repose demonstrates improved fluidity and therefore, improved handling property due to the larger particle size of the product.

The aerated bulk density of the granular product of 2-hydroxynaphthalene-3-carboxylic acid may be 0.6–0.85 g/cc, preferably, 0.7–0.8 g/cc. The packed bulk density may be 0.73–0.88 g/cc and preferably, 0.78–0.85 g/cc.

Further, the compression ratio of the granular product of the present invention, which is the value obtained according to the following formula:

(packed bulk density—aerated bulk density)/packed bulk density× 100 may be equal to or less than 10%, preferably, equal to or less than 7%. The compression ratio of the conventional powdery 2-hydroxynaphthalene-3-carboxylic acid having a small particle size is as high as 20–50% showing that the difference between the aerated bulk density and the packed bulk density is significant. This demonstrates that when the conventional powdery 2-hydroxynaphthalene-3-carboxylic acid is packed in a standard container, there is significant amount of air spaces between the particles. To the contrary, the low compression ratio, as low as less than 10%, of the granular product of the present invention demonstrates the improved filling property, that is, the product filled even without tapping vibration or impact contains only small amount of air spaces.

According to the present invention, the granular product of 2-hydroxynaphthalene-3-carboxylic acid may preferably be charged equal to or less than 0.02 μC/g. Due to the small amount of electrostatic charge, adhering of the product to the container or plastic-bag due to the electrostatic force is suppressed and therefore, operability of the product is improved.

The granular product of 2-hydroxynaphthalene-3-carboxylic acid of the present invention may be prepared by dry compressing powdery 2-hydroxynaphthalene-carboxylic acid, pulverizing the compressed material and classifying the pulverized material. The starting material, 2-hydroxynaphthalene-3-carboxylic acid may be any of those obtained by a conventional method. For example, according to the Kolbe-Schmidt reaction disclosed in Japanese Patent Publication (KOKOKU) No. 53296/1981, 2-hydroxynaphthalene-3-carboxylic acid may be prepared by aciding out 2-hydroxynaphthalene-3-carboxylic acid alkaline metal salt at 80–100° C., and if desired, purifying. In this method, the acid used in the aciding out step is not particularly limited, and an inorganic or organic acid may be used. Examples of inorganic acids include binary acid (hydrogen acid) such as hydrochloric acid and hydrofluoric acid, oxo acids such as nitric acid, sulfuric acid, phosphoric acid and perchloric acid. Examples of organic acids include fromic acid, acetic acid and phenol. The pH in the aciding out step may be adjusted to 1–4 by means of the acid as above.

According to the present invention, thus obtained powdery 2-hydroxynaphthalene-3-carboxylic acid is dry compressed, the compressed material is then pulverized and classified to give the granular product of 2-hydroxynaphthalene-3-carboxylic acid of the present invention.

Generally, the term "granulating" or "granulation" represents a process to provide granular product consisting of particles each having almost same size and shape, from a starting material in the form of powder, melt or aqueous solution. There are many known granulation processes such as extrusion, spray dry, milling, mixing and fluidized bed granulation. In the process of the present invention, the powdery 2-hydroxynaphthalene-3-carboxylic acid is dry compressed with a compressor to give compressed material, the compressed material is then pulverized and classified to give granular product of the present invention. This type of procedure is generally called as dry milling granulation.

The dry compressing step may be carried out mechanically under compression pressure of 0.2–2.0 ton/cm. When the compression pressure is less than 0.2 ton/cm, the bonding force among the fine particles constituting the resulting granule becomes weak and the granule may easily be degraded. When the pressure is over 2.0 ton/cm, the bonding force becomes too strong and the dissolution property of the granule is spoiled. The roll used in the dry compressing step may preferably be corrugated roll or smooth slit roll.

The compressed material obtained by mechanical compression is then pulverized by means of a mill and then classified to give granular product with certain particle characteristics. The mill used in this step may be, for example, roll mill, medium mill, gas flow mill, shearing and grinding mill, and the like, and hammer type high speed rotary impact mill is preferably used.

The pulverized granules are then classified. The classifying step may generally be carried out according to a known process, for example, by means of a mesh screen of suitable size. The smaller particles removed by the classifying step may be returned to the compressing step, and the larger particles may be returned to the pulverizing step. Accordingly, the present process can prepare 2-hydroxynaphthalene-3-carboxylic acid with an excellent yield.

According to the present invention, due to the high pressure in the granulating process, the primary particles constituting the granule firmly agglomerate such that the particles are attracted by van der Waals force and electrostatic force each other. This situation is different from those obtained by conventional wet extrusion granulation wherein the primary particles constituting the granule are associated due to surface tension of the binder component. Therefore, the granular product of 2-hydroxynaphthalene-3-carboxylic acid obtained according to the present invention is strong enough to resist against impact stress and is dissolved in a medium quite easily, and therefore, is excellent in operability.

According to the present invention, the powdery 2-hydroxynaphthalene-3-carboxylic acid having a small average particle size used as starting material may be any of prepared by a conventional method and employed without adjusting water content. Accordingly, the step adding water to the starting powdery material, which was essential for the conventional wet extrusion granulation process, is no longer required and therefore, the process of the present invention is suitable for large scale production. In the present specification, the term "dry compressing" represents the step to compress the material without adding any binder component such as water, and does not mean that the starting material does not contain water at all. It is preferable that water content of the starting material, powdery 2-hydroxynaphthalene-3-carboxylic acid is less than 12%, more preferably less than 6%. By dry compressing of powdery 2-hydroxynaphthalene-3-carboxylic acid containing only small amount of water, granular product with high impact strength and good solubility described as above can be obtained.

The granular product of 2-hydroxynaphthalene-3-carboxylic acid of the present invention may be employed as an intermediate for preparing pigments or dyes.

The present invention is further illustrated by means of the attached examples.

EXAMPLE 1

Powdery 2-hydroxynaphthalene-3-carboxylic acid having a small particle size (approx. 40–70 μm; water content: 0.07%) prepared by the conventional Kolbe-Schmitt reaction was subjected to mechanical compression with a simple compression granulator under the conditions shown in table 1 to provide compressed material (samples 1–3). The compressing pressure was determined by adjusting roll speed and feeding speed of powdery 2-hydroxynaphthalene-3-carboxylic acid to the rolls (adjusted by screw speed) over the constant diameter of the rolls and distance between the rolls. Thus obtained compressed material was then pulverized by means of hammer type high speed rotating impact mill and classified with a series of mesh screens to provide granular product of 2-hydroxynaphthalene-3-carboxylic acid having particle properties shown in the table 2 (samples 1-1–1-8, samples 2-1–2-8, and samples 3-1–3-8).

Hardness, degradation ratio, dissolution time and dust dispersion of the samples are shown in table 3.

EXAMPLE 2

The above prepared samples were mixed as follows to give samples 1-9 and 2-9. The ratios were designed to imitate actual product.

Sample 1-9: No.1-2(8.21%), No.1-3(13.64%), No.1-4 (13.26%), No.1-5(42.68%), No.1-6(22.21%)

Sample 2-9: No.2-2(12.57%), No.2-3(14.73%), No.2-4 (15.27%), No.2-5(39.46%), No.2-6(17.97%)

In addition to the above, untreated powdery 2-hydroxynaphthalene-3-carboxylic acid (the starting material: average particle size of about 40–70 μm) was subjected to evaluation as sample 4.

Powder properties, dissolution time and dust dispersion of the samples are shown in table 4.

The properties of the samples were evaluated as follows according to above DEFINITIONS.

Particle size of the product was determined by screening the sample with the sieves described as above using a shaker (Iida Seisaku Sho ES-65), and weighting the residues on the respective sieves and those passed the last sieve. The average particle size was determined according to the formula described in the DEFINITIONS as above.

Angle of repose, spatula angle, and bulk density of the samples were evaluated. The evaluation was carried out with Powder Tester PT-N type, Hosokawa micron Co. according to the instruction provided by the manufacturer. In addition, the angle of the composition deposited on the spatula was measured to give spatula angle.

Hardness

Hardness was measured by means of simplified hardness meter (Tsutsui Rikagaku Kikai Co.) as follows. Firstly, the pointer of the hardness meter was confirmed to be at the position 0. The sample (i.e. 2-hydroxynaphthalene-3-carboxylic acid granule) was put on the sample stage with a tweezers and the head of the push bar was contacted to the center of the sample granule. Then, weight was loaded by operating handle of the hardness meter and the value at which the granule was broken was recorded. The value was determined 10 or more times per one sample and the average was calculated.

Hardness of the sample granule having a particle size of less than 0.3 mm could not be measured because it was difficult to put the same at the correct location.

Degradation Ratio

Degradation ratio was determined by means of defacement tester (Kayagaki Irika Kogyo Co.) as follows. 10 g of the sample was weighed and sieved with 60M-mesh screen (sieve having aperture of 0.25 mm) for 1 minute by means of the same shaker used for particle size determination (Iida Seisakusyo, ES-65). The residue on the sieve was loaded into the defacement tester having inner diameter of 27 cm and thickness of 4 cm and was subjected to impact stress at 25 rpm for 3 minutes. After that, the resulting samples were sieved again with the 60M-mesh screen for 1 minute. The degradation ratio (%) was calculated from the amount of residue on the mesh before impact stress ($W_1$) and those after impact stress ($W_2$) according to the following formula:

$$\text{Degradation ratio } (\%) = (W_1 - W_2)/W_1 \times 100$$

The granular products having a particle size of less than 0.3 mm were qualified as those already degraded and were not subjected to this evaluation.

Dissolution Time 10 g of the granular sample of 2-hydroxynaphthalene-3-carboxylic acid was weighed and added to 104 g of 5% aqueous sodium hydroxide and stirred The time required to dissolve the sample completely (visually monitored) was recorded.

Evaluation of Dust Dispersion

Dust dispersion tester was used for this evaluation. 50 g of the granular sample was slid down along the slope of 60° for 50 cm. When the composition reached to the bottom of the slope, the height and distance to which the dust flew were measured. When the distance was over 70 cm and height was over 50 cm, they were qualified as "over".

COMPARATIVE EXAMPLE 1

Wet Extrusion Granulation

The same powdery 2-hydroxynaphthalene-3-carboxylic acid used in Example 1 (100 parts per weight) was added with 25 parts per weight of water and centrifuged to adjust the water content being 22%. The mixture was granulated by extrusion granulator having dies of 1.0 mm aperture to give granular product of 2-hydroxynaphthalene-3-carboxylic acid having an average particle size of 344 μm. The particle characteristics of the obtained product are shown in table 5 and evaluation results are shown in table 6.

COMPARATIVE EXAMPLE 2

Granular product of 2-hydroxynaphthalene-3-carboxylic acid having an average particle size of 280 μm was prepared by the same manner as comparative example 1 except for 25 parts per weight of water was replaced with 25 parts per weight of 20% aqueous methanol. The particle characteristics of the obtained product are shown in table 5 and evaluation results are shown in table 6.

COMPARATIVE EXAMPLE 3

Granular product of 2-hydroxynaphthalene-3-carboxylic acid having an average particle size of 340 μm was prepared by the same manner as comparative example 1 except for 25 parts per weight of water was replaced with 30 parts per weight of 20% aqueous methanol. The particle characteristics of the obtained granule are shown in table 5 and the evaluation results are shown in table 6.

Granular products obtained by dry compression in example 1 having an average particle size of over 150 μm and a hardness of over 70 g (Nos. 1-1–1-5, Nos. 2-1–2-5 and Nos. 3-1–3-5) represented less than 3% of degradation ratio demonstrating that the products of the invention had excellent impact strength and were hardly degraded. The less than 15 minutes dissolution time demonstrated good workability. Further, the dust dispersion (distance) of the samples were less than 45 cm, demonstrating that the operability of the samples were excellent.

To the contrary, the dissolution time of those having an average particle size of less than 150 μm (Nos. 1-7, 1-8, Nos. 2-7, 2-8 and Nos. 3-7 and 3-8) were over 20 minutes, showing deteriorated workability. Further, the dust dispersion distances of those products were over 50 cm, demonstrating that the operability of the product was poor.

Samples 1-9 and 2-9 in example 2 were prepared by mixing the granules having various particle sizes to imitate the actual products. Both of angle of repose and spatula angle of these samples were reduced, showing that fluidity of these samples were improved than those untreated fine particles (sample 4). The compression ratios of these samples were less than 7%, showing good filling ability. Further, the short dissolution time and small dust dispersion distance of the samples demonstrated that the granular products were excellent in workability and operability.

In the comparative examples 1–3, the granular products of 2-hydroxynaphthalene-3-carboxylic acid were prepared by extrusion granulation. The products having even more than 150 μm of average particle size represented less than 20 g of hardness showing that they were easily degraded. The granule of comparative example 1 was degraded when it was caught by tweezers and therefore, hardness of the product could not be determined. All of the granular products of comparative examples showed more than 10% of degradation ratio.

TABLE 1

| Sample No. | Type of roll | roll speed (rpm) | screw speed (rpm) | pressure (ton/cm) |
|---|---|---|---|---|
| 1 | Smooth slit | 16.3 | 83 | 0.59 |
| 2 | corrugated | 21.3 | 86 | 0.52 |
| 3 | corrugated | 21.3 | 92 | 0.72 |

TABLE 2

| Sample No. | average particle size (μm) | particle distribution (%) | | | | | | |
|---|---|---|---|---|---|---|---|---|
| | | ~1800 | 500~1180 | 297~500 | 180~297 | 106~180 | 74~106 | 74~ |
| 1-1 | 1133 | 94.5 | 3.2 | 0.3 | 0.5 | 0.4 | 0.1 | 1.1 |
| 1-2 | 1073 | 85.6 | 12.1 | 0.2 | 0.5 | 0.3 | 0.0 | 1.3 |
| 1-3 | 684 | 28.0 | 70.1 | 0.3 | 0.5 | 0.1 | 0.0 | 1.0 |
| 1-4 | 480 | 0.2 | 93.9 | 1.4 | 1.0 | 0.6 | 0.9 | 2.0 |
| 1-5 | 439 | 0.1 | 75.2 | 19.1 | 1.5 | 0.9 | 1.1 | 2.1 |
| 1-6 | 235 | 0.0 | 0.0 | 52.4 | 41.6 | 1.9 | 1.1 | 2.9 |
| 1-7 | 123 | 0.0 | 0.0 | 0.0 | 35.6 | 45.7 | 6.1 | 12.6 |
| 1-8 | 81 | 0.0 | 0.1 | 0.0 | 0.5 | 14.6 | 19.6 | 65.2 |
| 2-1 | 1099 | 90.3 | 5.7 | 1.1 | 0.3 | 0.6 | 0.1 | 1.9 |
| 2-2 | 1030 | 80.3 | 15.8 | 0.5 | 0.3 | 0.5 | 0.0 | 2.5 |
| 2-3 | 644 | 23.4 | 72.7 | 0.7 | 0.3 | 0.2 | 0.1 | 2.6 |
| 2-4 | 477 | 0.1 | 93.5 | 1.6 | 0.6 | 0.8 | 0.1 | 3.3 |
| 2-5 | 437 | 0.0 | 74.8 | 19.8 | 1.1 | 0.7 | 0.2 | 3.4 |
| 2-6 | 240 | 0.0 | 0.0 | 57.3 | 36.2 | 2.5 | 0.2 | 3.9 |
| 2-7 | 132 | 0.0 | 0.0 | 0.0 | 44.6 | 40.3 | 6.5 | 8.6 |

TABLE 2-continued

| Sample No. | average particle size (μm) | particle distribution (%) | | | | | | |
|---|---|---|---|---|---|---|---|---|
| | | ~1800 | 500~1180 | 297~500 | 180~297 | 106~180 | 74~106 | 74~ |
| 2-8 | 61 | 0.0 | 0.0 | 0.0 | 1.4 | 15.0 | 17.0 | 66.6 |
| 3-1 | 1110 | 91.6 | 5.2 | 0.4 | 0.4 | 0.5 | 0.3 | 1.7 |
| 3-2 | 1062 | 84.4 | 12.6 | 0.5 | 0.3 | 0.3 | 0.3 | 1.7 |
| 3-3 | 613 | 19.4 | 75.9 | 0.8 | 0.8 | 0.3 | 0.2 | 2.7 |
| 3-4 | 479 | 0.3 | 93.5 | 1.1 | 1.0 | 1.1 | 0.8 | 2.3 |
| 3-5 | 431 | 0.0 | 71.7 | 22.4 | 1.6 | 1.4 | 1.4 | 1.6 |
| 3-6 | 247 | 0.0 | 0.0 | 61.4 | 33.9 | 1.7 | 1.2 | 1.8 |
| 3-7 | 148 | 0.0 | 0.0 | 0.0 | 62.1 | 30.0 | 2.1 | 5.8 |
| 3-8 | 69 | 0.0 | 0.3 | 0.2 | 1.2 | 23.6 | 21.1 | 53.7 |

TABLE 3

| Sample No. | hardness (g) | degradation ratio (%) | dissolution time (min.) | dust distribution (cm) | |
|---|---|---|---|---|---|
| | | | | distance | height |
| 1-1 | 610 | 0.94 | 14.00 | 30 | 20 |
| 1-2 | 400 | 0.88 | 10.17 | 35 | 25 |
| 1-3 | 343 | 0.95 | 9.17 | 40 | 25 |
| 1-4 | 281 | 0.80 | 6.00 | 40 | 20 |
| 1-5 | 177 | 0.70 | 5.72 | 45 | 25 |
| 1-6 | — | — | 13.50 | 50 | 20 |
| 1-7 | — | — | 58.00 | 70 | 25 |
| 1-8 | — | — | 38.83 | 70 | 50 |
| 2-1 | 355 | 1.20 | 14.33 | 30 | 20 |
| 2-2 | 265 | 1.21 | 11.83 | 35 | 25 |
| 2-3 | 206 | 0.80 | 9.83 | 40 | 25 |
| 2-4 | 149 | 1.11 | 7.67 | 40 | 20 |
| 2-5 | 118 | 1.00 | 9.33 | 45 | 25 |
| 2-6 | — | — | 8.08 | 50 | 20 |
| 2-7 | — | — | 22.09 | 70 | 25 |
| 2-8 | — | — | 36.67 | 70 | 50 |
| 3-1 | 355 | 0.72 | 14.33 | 30 | 20 |
| 3-2 | 265 | 0.68 | 11.17 | 35 | 25 |
| 3-3 | 206 | 0.97 | 10.00 | 40 | 25 |
| 3-4 | 149 | 1.86 | 5.83 | 40 | 20 |
| 3-5 | 118 | 1.01 | 10.83 | 45 | 25 |
| 3-6 | — | — | 7.33 | 50 | 20 |
| 3-7 | — | — | 62.00 | 70 | 25 |
| 3-8 | — | — | 42.00 | 70 | 50 |

TABLE 4

| Sample No. | angle of repose (deg.) | spatula angle (deg.) | bulk density (g/cc) | | compression ratio (%) | dissolution time (min.) | dusts dispersion (cm) | |
|---|---|---|---|---|---|---|---|---|
| | | | aerated | packed | | | distance | height |
| 1-9 | 41.4 | 50.6 | 0.768 | 0.808 | 4.95 | 11.83 | 30 | 50 |
| 2-9 | 38.9 | 51.6 | 0.768 | 0.820 | 6.34 | 13.00 | 50 | 50 |
| 4 | 49.5 | 64.3 | 0.370 | 0.726 | 49.00 | 34.84 | over | over |

TABLE 5

| Sample No. | average particle size (μm) | particle distribution | | | | | | hardness (g) | degradation ratio (%) |
|---|---|---|---|---|---|---|---|---|---|
| | | ~1180 | 500~1180 | 297~500 | 180~297 | 106~180 | 74~106 | 74~ | | |
| Comp. Ex. 1 | 344 | 0.3 | 2.02 | 27.4 | 4.3 | 6.3 | 5.1 | 3.65 | — | 35.56 |
| Comp. Ex. 2 | 280 | 0 | 5.2 | 24.8 | 34.6 | 18.6 | 3.1 | 13.7 | 19 | 15.81 |
| Comp. Ex. 3 | 300 | 0.1 | 6.1 | 38.3 | 13.3 | 9.2 | 4.1 | 28.9 | 5 | 57.63 |

TABLE 6

| Sample No. | angle of repose (deg.) | spatula angle (deg.) | bulk density (g/cc) aerated | bulk density (g/cc) packed | compression ratio (%) | dissolution time (min.) | dusts dispersion distance | dusts dispersion height |
|---|---|---|---|---|---|---|---|---|
| Comp. Ex. 1 | 40.8 | 56.3 | 0.583 | 0.708 | 17.66 | 8.67 | 65 | over |
| Comp. Ex. 2 | 42.0 | 54.0 | 0.488 | 0.618 | 21.04 | 18.50 | 45 | over |
| Comp. Ex. 3 | 42.5 | 58.5 | 0.540 | 0.685 | 21.17 | 19.67 | 50 | over |

INDUSTRIAL APPLICABILITY OF THE INVENTION

According to the present invention, granular product of 2-hydroxynaphthalene-3-carboxylic acid with significantly suppressed dusting tendency can be prepared.

What is claimed is:

1. A granular product of 2-hydroxynaphthalene-3-carboxylic acid, characterized in that having an average particle size of equal to or more than 150 μm and a hardness of 70–3000 g.

2. The granular product of 2-hydroxynaphthalene-3-carboxylic acid according to claim 1, characterized in that the proportion of the particles which pass through a sieve with 74 μm of aperture to whole product is equal to or less than 14 wt %.

3. The granular product of 2-hydroxynaphthalene-3-carboxylic acid according to claim 1, characterized in that the degradation ratio is equal to or less than 3%.

4. The granular product of 2-hydroxynaphthalene-3-carboxylic acid according to claim 1, characterized in that the dissolution time determined by dissolving 10 g of the product in 104 g of 5% aqueous sodium hydroxide at an ambient temperature is less than 20 minutes.

5. The granular product of 2-hydroxynaphthalene-3-carboxylic acid according to claim 1, characterized in that the angle of repose is 35–45°.

6. The granular product of 2-hydroxynaphthalene-3-carboxylic acid according to claim 1, characterized in that the aerated bulk density is 0.6–0.85 g/cc, packed bulk density is 0.73–0.88 g/cc and compression ratio calculated as below:

(packed bulk density−aerated bulk density)/packed bulk density× 100 is equal to or less than 10%.

7. A process for preparing the granular product of 2-hydroxynaphthalene-3-carboxylic acid of claim 1, comprising the steps of dry compressing powdery 2-hydroxynaphthalene-3-carboxylic acid to give compressed material, pulverizing the compressed material to give granules and classifying the granules.

8. The process of claim 7, wherein the dry compressing is carried out at the pressure of 0.2–2.0 ton/cm.

9. The process of claim 7, wherein the water content of the powdery 2-hydroxynaphthalene-3-carboxylic acid is equal to or less than 12%.

* * * * *